United States Patent [19]

Fellingham et al.

[11] Patent Number: 5,191,795
[45] Date of Patent: Mar. 9, 1993

[54] ULTRASONIC DETECTOR

[75] Inventors: George H. Fellingham, San Jose; Lance B. Koll, Santa Clara; Timothy J. Hughes, Palo Alto, all of Calif.

[73] Assignee: Abbott Laboratories, Abbott Park, Ill.

[21] Appl. No.: 753,009

[22] Filed: Aug. 23, 1991

Related U.S. Application Data

[60] Continuation of Ser. No. 448,806, Dec. 11, 1989, abandoned, which is a continuation-in-part of Ser. No. 307,489 Feb. 6, 1989, Pat. No. 4,944,191, which is a division of Ser. No. 45,951, May 1, 1987, Pat. No. 4,821,558.

[51] Int. Cl.$^5$ .................. G01N 9/24; G08B 21/00
[52] U.S. Cl. ........................ 73/599; 340/621
[58] Field of Search .......... 73/599, 642, 19.1, 19.03; 310/316; 340/621; 367/903

[56] References Cited

U.S. PATENT DOCUMENTS

| | | | |
|---|---|---|---|
| 4,275,363 | 6/1981 | Mishiro et al. | 310/316 |
| 4,554,477 | 11/1985 | Ratcliff | 310/316 |
| 4,607,520 | 8/1986 | Dam | 73/19.03 |

Primary Examiner—Louis Arana
Attorney, Agent, or Firm—Christensen, O'Connor, Johnson & Kindness

[57] ABSTRACT

An ultrasonic detector for detecting air in a fluid passage is disclosed. The detector comprises a transmitting crystal and complementary receiving crystal disposed around the fluid passage. A sweep oscillator is used to apply a variable-frequency signal to drive the transmitting crystal into resonance so that a burst of ultrasonic energy is released therefrom. The swept frequency range encompasses the resonant frequency of the transmitting crystal, ensuring that it resonates. If there is fluid in the passage, the ultrasonic energy causes a relatively high voltage to develop across the receiving crystal. Air in the passage attenuates transmission of the ultrasonic energy so that a low voltage signal is developed across the receiving crystal. A sensor circuit connected to the receiving crystal monitors the signal developed thereacross and in response to the magnitude of the signal, asserts a signal that indicates whether there is air or fluid in the passage.

28 Claims, 8 Drawing Sheets

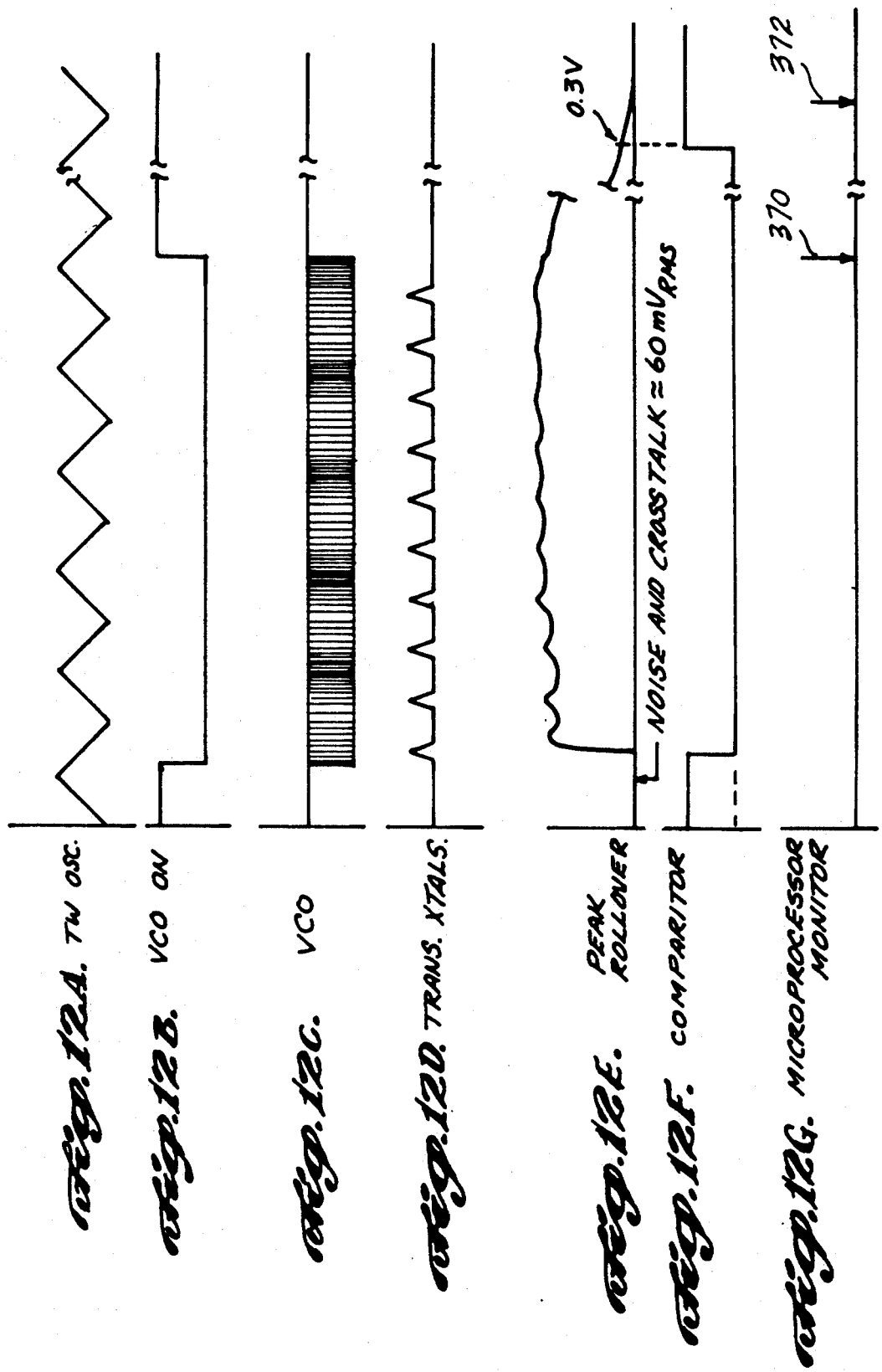

ULTRASONIC DETECTOR

RELATIONSHIP TO OTHER APPLICATIONS

This application is a continuation of application Ser. No. 07/448,806 filed Dec. 11, 1989 now abandoned which was a continuation-in-part of application Ser. No. 07/307,489 filed Feb. 6, 1989 now U.S. Pat. No. 4,944,191, which is a divisional of application Ser. No. 07/045,951 filed May 1, 1987, which issued as U.S. Pat. No. 4,821,558 on Apr. 18, 1989.

FIELD OF THE INVENTION

The present invention relates to a detector which is adapted to detect whether a gas or a liquid is present in a fluid delivery conduit. The detector of the present invention is particularly suited for use as a low cost air-in-line detector in intravenous flow control equipment for delivering intravenous fluid to patients.

BACKGROUND OF THE INVENTION

In administering intravenous liquid-state fluid to patients, it is important to monitor the fluid being administered for the presence of air because if air is infused into a patient, an embolism can occur. Air can be introduced into a system through a leak in a tubing connector, through a crack in the equipment, or when the container from which the fluid is delivered is emptied. In some cases, particularly with flexible walled IV containers, the container is not completely filled at the factory, leaving an air space. This air may be infused into the patient if the fluid is delivered with a volumetric pump. There have been some attempts at using optical detectors to monitor intravenous fluids for the presence of bubbles. However, optical detectors can often produce false air-in-line signals when the tube or conduit is actually filled with liquid. Some IV fluids scatter and do not focus light, particularly IV fluids which contain particulates. Some IV fluids may be semi-opaque. The result is that the detector cannot distinguish between a liquid filled and an air filled conduit.

Furthermore, optical detectors of the type described above require the use of clear plastics in the liquid conduit. However, many useful medical grade plastics and intravenous liquids are not clear, so an optical detector cannot be used with them.

SUMMARY OF THE INVENTION

The present invention is an ultrasonic liquid-state fluid detector comprising an ultrasonic sound generator and an ultrasonic sound receiver spacedly disposed from one another so as to receive a liquid carrying member therebetween. The sound generator and receiver each include a substrate and a layer of conductive material in the substrate. The conductive layer has at least two regions that are electrically isolated from each other. A piezoelectric crystal is placed in electrical contact over at least a portion of the first region of the conductive layer. A conductive member extends between the piezoelectric crystal and the second region of the conductive layer. An electrical signal having a frequency at the resonant frequency of the piezoelectric crystal on the sound generator can be applied between the first and second regions of the sound generator conductive layer to cause ultrasonic sound to be generated. Ultrasonic sound can be received by the piezoelectric crystal on the sound receiver and can be electrically detected by monitoring the electric signal produced between the first and second regions of the conductive layer on the sound receiver.

Other aspects of the present invention include an air-in-line detection assembly including an elastomeric member with a fluid passage therethrough and having a pair of resilient lobes extending in opposite direction therefrom and having a fluid passageway therethrough. An ultrasonic sound generator and an ultrasonic sound receiver are spacedly positioned from and facing each other. The elastomeric member is positioned between the sound generator and receiver and the sound generator and receiver are spaced such that the lobes are compressed inwardly of the elastomeric member so that each lobe maintains close contact with one of the sound generator and receiver. The present invention provides an ultrasonic detector which is reliable, wash to manufacture, and allows the member, through which fluid flows, to be readily engaged with and/or disengaged from the ultrasonic detector. These and other advantages of the present invention will become apparent from the disclosure which follows.

BRIEF DESCRIPTION OF THE DRAWINGS

FIGS. 12A-G are timing diagrams illustrating the signals asserted during the operation of the microprocessor of FIG. 10 and the alternative air-in-line detector circuit of FIG. 11 of this invention.

DETAILED DESCRIPTION OF THE PREFERRED EMBODIMENT

Figure 3:
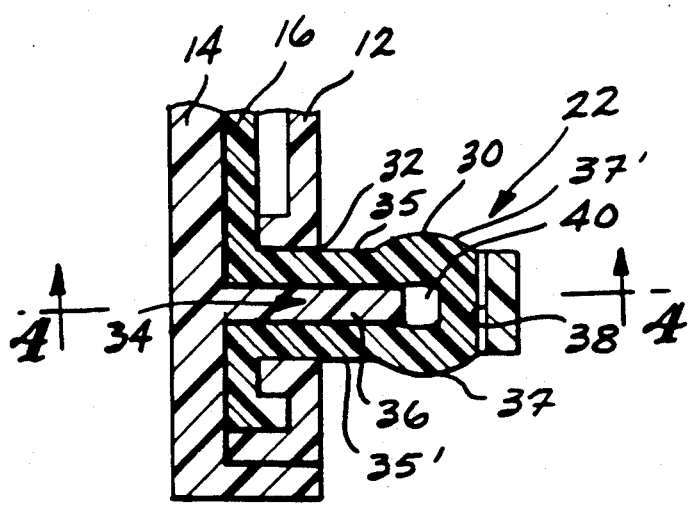
FIG. 3 is a cross section taken along the plane of line III—III of FIG. 1.
Figure 4:
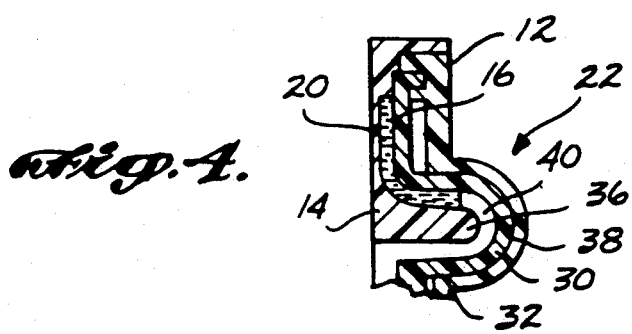
FIG. 4 is a cross section taken along the plane of line IV—IV of FIG. 3.

The present invention is an ultrasonic air-in-line detector system particularly adapted for use with a disposable intravenous fluid pumping cassette disclosed in U.S. patent application Ser. No. 045,959 entitled Disposable Fluid Infusion Pumping Chamber Cassette, filed by Giovanni Pastrone on May 1, 1987, the disclosure of which is incorporated herein by reference. The pumping cassette 10 includes a rigid face member 12 and a rigid back member 14 with elastomeric member 16 positioned therebetween (FIGS. 3-4). The cassette includes an inlet 18 to receive fluid, understood throughout this application to be liquid-state fluid, from a fluid source (not shown) and an outlet (not shown) for delivering fluid at a positive pressure to the patient. Between the inlet and outlet is a fluid path 20 (FIG. 4) through air-in-line detection means 22, 24 which project outwardly from the surface of face member 12. Air-in-line detection means 22 engages an ultrasonic detector 26. Air-in-line detection means 24 engages ultrasonic detector 28.

Fluid pumped through cassette 10 passes through both air-in-line detection means 22 and 24, and ultrasonic detectors 26 and 28 are adapted to detect the presence of air being pumped through the cassette to prevent air from being pumped into the patient. Air-in-line detection means 22 and 24 are series-connected; fluid flows first through detection means 22 and then through detection means 24. Since ultrasonic detector 26 engages air-in-line detection means 22 that is closer to the fluid source, it is referred to as the "empty detector." Ultrasonic detector 28, which engages air-in-line detection means 24 that is closer to the patient, is referred to as the "bubble detector."

Air-in-line detection means 22 is identical to air-in-line detection means 24, so only one of them will be described in detail. Likewise, ultrasonic detector 26 is structurally the same as ultrasonic detector 28, so only the former will be described.

Air-in-line detection means 22 includes a pocket 30 formed integrally as part of elastomeric member 16. Pocket 30 extends through an opening 32 in face member 12 and projects outwardly beyond the surface of face member 12. (FIGS. 1, 3, 3A, and 4.) Pocket 30 has a hollow recess 34 within it which is formed within two sidewalls 35 and 35' and an arcuate endwall 38. A finger 36 projects from the inner surface of back member 14 into recess 34 and fits interferingly between sidewalls 35 and 35', but does not contact endwall 38. Rather, a fluid passage 40 is formed between the inside surfaces of endwall 38 and the perimeter of finger 36 which forms part of the fluid path 20 through the cassette. Fluid passage 40 allows the fluid flowing through fluid path 20 in the cassette to loop outwardly from the surface of face member 12 so that any air in the fluid path can be detected by an ultrasonic detector 26 (or 28) outside of the cassette. Ultrasonic detectors 26 and 28 are to be mounted on a cassette driver, a nondisposable item, whereas the cassette is inexpensive and disposable after each use.

Ultrasonic detector 26 includes two substantially mirror image housing portions 42 and 44. Housing member 42 is generally L-shaped and is joined to the mirror image L-shaped housing 44 at the bottom of the L's so as to form a U-shaped housing assembly with recess 46 between the arms of the U adapted to receive air-in-line detection means 22. On one side of recess 46, housing portion 42 has an opening 48, while on the other side of recess 46, housing portion 44 has an opening 50. Housing members 42 and 44 are hollow, each containing a passage 52 for the necessary electrical pins described below. Positioned across opening 48 is an ultrasonic generator 54, facing an ultrasonic receiver 56 positioned in opening 50 across recess 46. Ultrasonic generator 54 is structurally the same as ultrasonic receiver 56, so only ultrasonic generator 54 will be described.

Ultrasonic generator 54 (FIGS. 5-7) includes a substrate 58, preferably made of glass or ceramic coated on one side with a conductive layer 60, preferably on a layer of gold. Conductive layer 60 includes three sections 62, 64, and 66 which are electrically isolated from one another with a gap 68 between regions 62 and 64 and between regions 64 and 66, and a gap 70 which divides regions 60 and 62. A crystal 72 made of a piezoelectric material such as lead zirconate titanate (PZT), preferably a Murata P7 or Valpey-Fisher PZT-5H piezoelectric crystal, is adhered to conductive layer 60 with a conductive epoxy adhesive, and is positioned such that one face of crystal 72 overlays at least a portion of layer region 64, but the same face does not contact layer region 66. A conductive filament 74 extends from the opposite face of crystal 72 to layer region 66, establishing an electrical connection therebetween.

Figure 1:
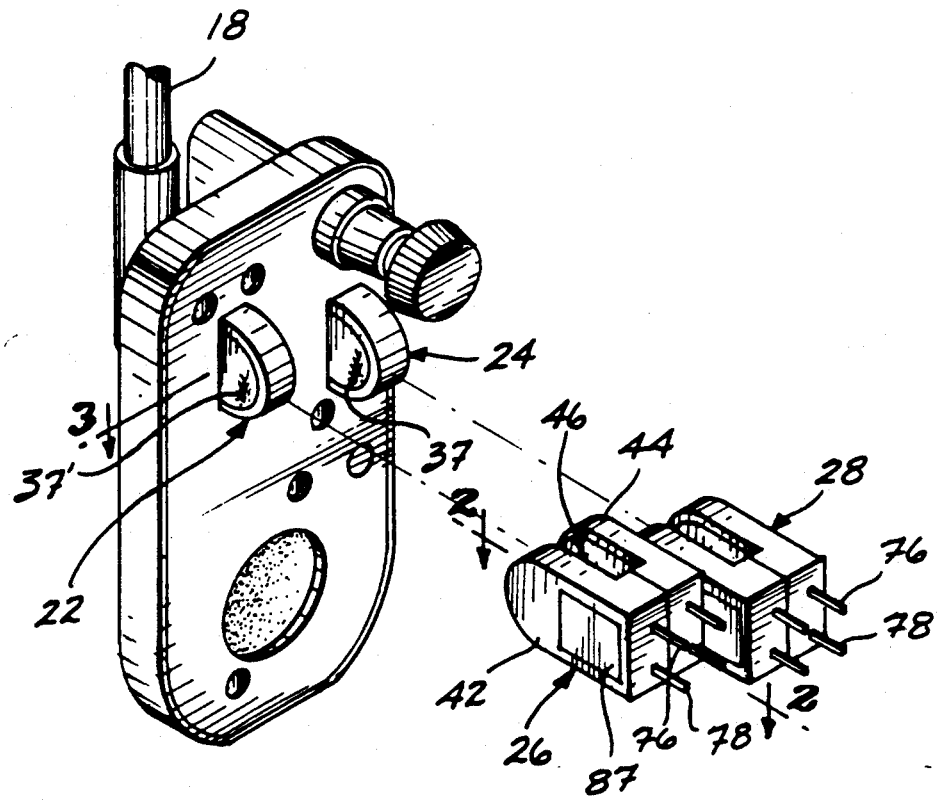
FIG. 1 is a perspective view of a disposable pump cassette featuring one aspect of the present invention together with ultrasonic detectors of the present invention.
Figure 2:
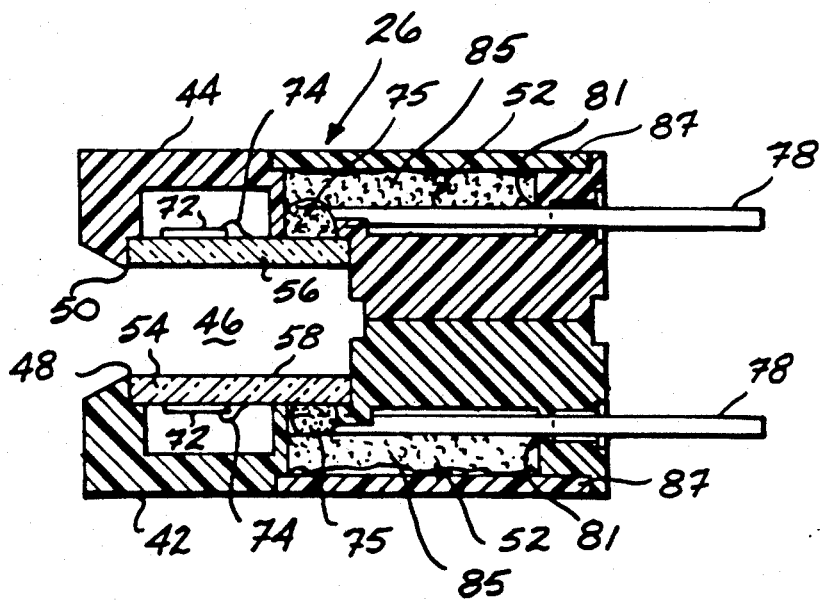
FIG. 2 is a cross section of one of the ultrasonic detectors of FIG. 1 taken along the plane of line II—II of FIG. 1.
Figure 3A:
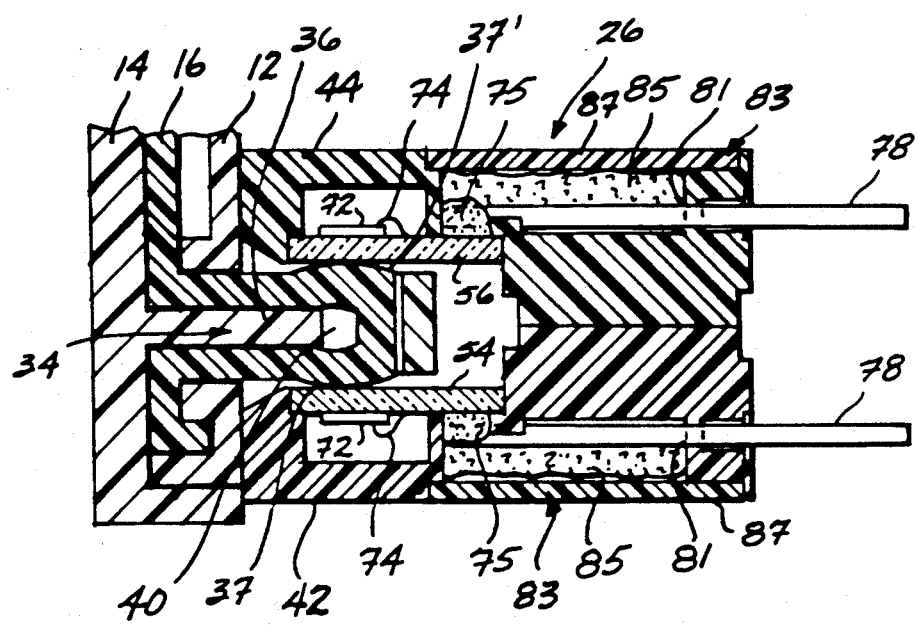
FIG. 3A is a cross-sectional view of the components of FIGS. 2 and 3 shown in engaged position.
Figure 5:
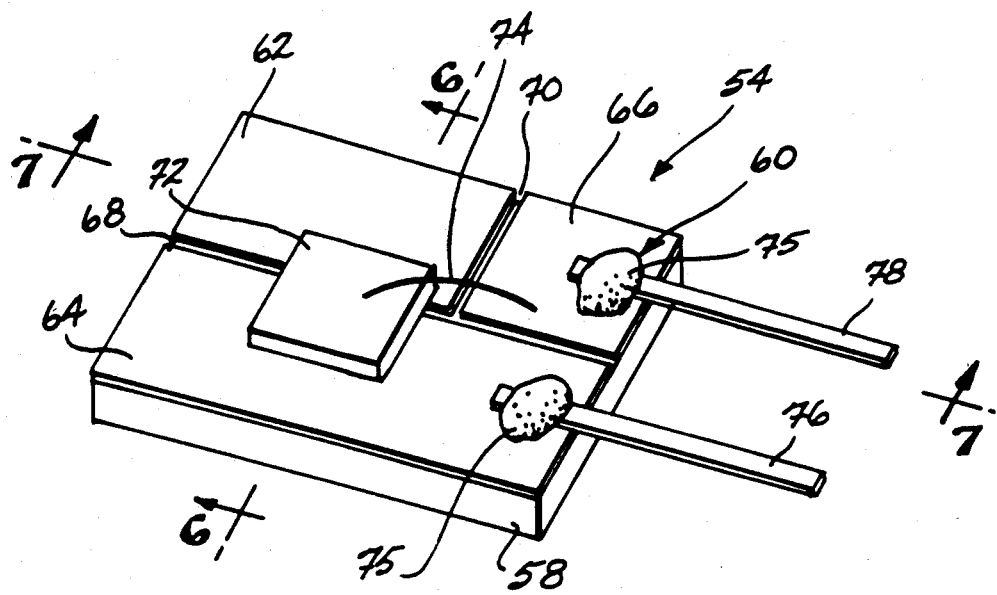
FIG. 5 is a perspective view of the ultrasonic sound generator and/or the ultrasonic sound receiver employed in the ultrasonic detector of FIG. 2.
Figure 6:
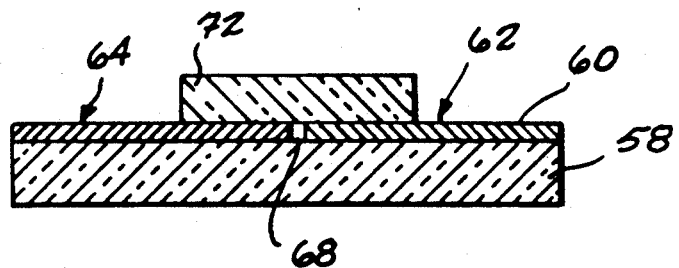
FIG. 6 is a cross section taken along the plane of lines VI—VI of FIG. 5.
Figure 7:
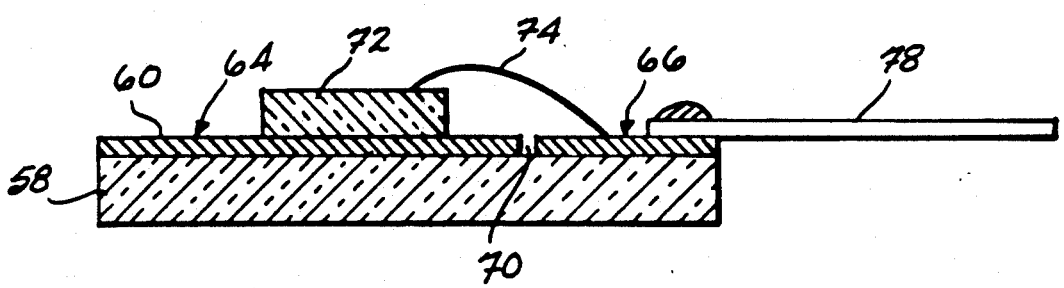
FIG. 7 is a cross section taken along the plane of line VII—VII of FIG. 5.

An electrically conductive pin 76 is electrically connected to layer region 64 while a pin 78 is electrically connected to layer region 66. This electrical connection is accomplished by gluing each pin to the appropriate region with an electrically conductive epoxy adhesive 75 (FIGS. 2, 3A, and 5). When the assembly shown in FIGS. 5-7 is used as an ultrasonic generator, an electrical signal having a frequency the same as the resonant frequency of piezoelectric crystal 72 is applied to crystal 72 across leads 76 and 78 with the circuitry described below to conductive regions 60 and 64 through filament 74, to excite the crystal to emit a high frequency sound. As shown in FIGS. 1, 2, and 3A, pins 76 and 78 extend out of housings 42 and 44. Housings 42 and 44 are mounted on a printed circuit board (not shown) through which pins 76 and 78 extend to connect to the circuitry described below.

To assemble an ultrasonic generator or receiver, crystal 72 is mounted on substrate 58 by conductive adhesive. Filament 74 is attached as described above. Substrate 58 is then positioned in the opening 48 (or 50). Pin 78 (or 76) is inserted through a narrow aperture 81 (FIG. 2) in the rear of housing 42 (or 44) until the proximal end of the pin is positioned over the appropriate conductive region on the substrate. Through a large opening 83 (FIGS. 2 and 3A) in the side of housing 42 (or 44), conductive adhesive 75 is applied to adhere the proximal end of each pin 78 (and 76) to the appropriate conductive region on the substrate. These pins 76 and 78 are "potted" within housing 42 and 44 by filling the housings with non-conductive epoxy adhesive 85 (FIGS. 2 and 3A). Thus, openings 81 and adhesive 85 hold pins 76 and 78 immovably within housings 42 and 44 so they cannot be dislodged from electrical contact with substrates 56 and 58.

Openings 83 in housings 42 and 44 are covered by covers 87 (FIG. 1) before adhesive 85 sets. Ultrasonic detectors 26 and 28 are then mounted on a printed circuit board (not shown) through which pins 76 and 78 extend. The distal ends of pins 76 and 78 are then soldered to make electrical connection with the circuitry described below on the printed circuit board. To function as an ultrasonic receiver 56, the assembly shown in FIGS. 5-7 receives the ultrasonic sound generated by ultrasonic generator 54. The ultrasonic vibration is picked up by a receiving crystal 72 and is converted to an electrical signal which is transmitted across filament 74 and through layers 60 and 64 to pins 76 and 78 (FIG. 1) where the high frequency electrical signal can be converted and amplified by the circuitry described below into a usable signal to sound an alarm in the event that air is present in fluid passage 40.

Elastomeric pocket 30 has two resilient lobes 37, 37' (FIGS. 1 and 3) which extend outwardly from sidewalls 35. The width of pocket 30 between lobes 37, 37' is somewhat less than the width of recess 46 between ultrasonic generator 54 and ultrasonic receiver 56 so that lobes 37 and 37' are compressed inwardly toward each other when air-in-line detection means 22 is inserted into ultrasonic detector 26 as shown in FIG. 3A. This insures that there will be good acoustic contact between ultrasonic generator 54 and pocket 30 and between ultrasonic receiver 56 and pocket 30.

This arrangement also allows the air-in-line detection means 22 to be inserted and withdrawn easily from recess 46. As shown in FIG. 3A, crystals 72 and 72' align with fluid passage 40 so that an ultrasonic signal is transmitted across fluid passage 40 when air-in-line detection means 22 is inserted into recess 46. The transmission of ultrasonic sound between ultrasonic generator 54 and ultrasonic receiver 56 is greatly enhanced when a liquid is present in passage 40. But when air is present in passage 40, the transmission of ultrasonic sound through fluid passage 40 is attenuated. This difference in ultrasonic sound transmission is detected by ultrasonic receiver 56. When air is present, the signal from ultrasonic receiver 56 drops. When a signal drops, an alarm (not shown) is sounded to stop the pumping of fluid through the cassette if the cassette is in the fluid delivery cycle.

As disclosed in co-pending application, Ser. No. 045,959, entitled Disposable Fluid Infusion Pumping Chamber Cassette, filed by Giovanni Pastrone on an even date herewith, the ultrasonic detectors and air-in-line detectors disclosed herein can be used also to check the integrity of several of the cassette components when the cassette is not in the fluid delivery part of its pumping cycle.

As indicated above, ultrasonic detectors 26 and 28 are parts of a nondisposable cassette driver, and cassette 10 is a disposable item. As cassette 10 is mounted on the driver, air-in-line detection means 22 and 24 slide easily into recesses 46 in ultrasonic detectors 26 and 28, but nonetheless intimate sound transmitting contact is achieved between each air-in-line detection means and its associated detector through lobes 37 and 37'. Lobes 37, 37' deflect inwardly as an air-in-line detector is slid into a recess 46, creating the desired contact, but the lobes do not interfere with the sliding insertion of the air-in-line detectors into the ultrasonic detectors.

Figure 8:
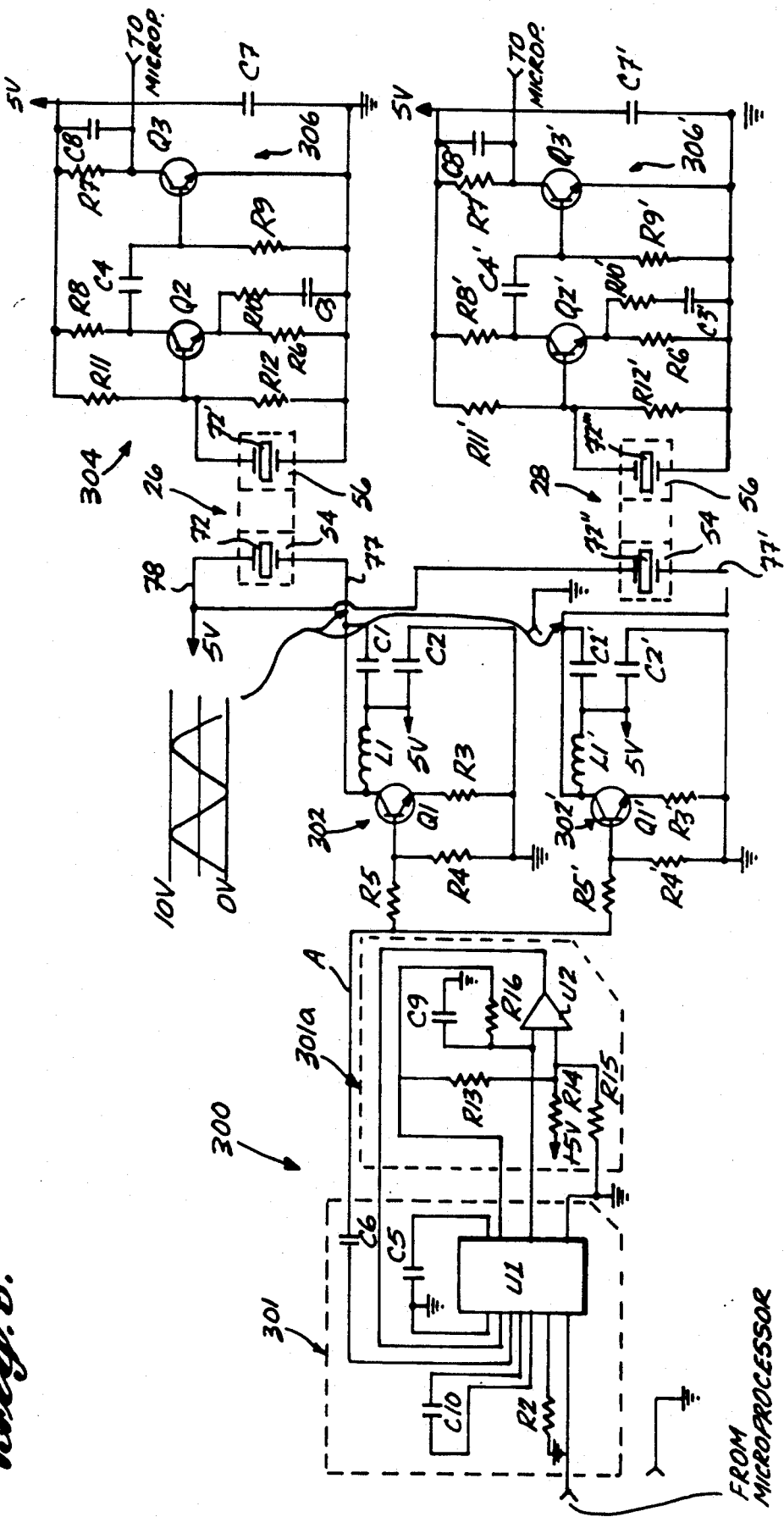
FIG. 8 is a schematic diagram of an embodiment of an air-in-line detection circuit of the present invention.

An air-in-line detection circuit 298 for the cassette driver of the present invention is illustrated in FIG. 8. The transmitting crystals 72 and 72'' of ultrasonic detectors 26 and 28, respectively, are controlled by a pair of amplifier circuits 302 and 302'. Amplifier circuits 302 and 302' are driven, in turn, by a sweep oscillator 300 which includes a voltage controlled oscillator 301 and a triangle wave oscillator 301a.

Each crystal (72-72''') will resonate at a variety of frequencies, but each has several peak resonating frequencies including one having a nominal value of about 5.00 MHz. However, the resonant frequency of a given crystal can vary from the nominal values. Furthermore, the resonant frequency of a crystal can shift when it is mounted on a substrate 58. To reduce the difference between the resonant frequencies of transmitting and receiving crystals, each pair of such crystals should be cut from the same piece of piezoelectric material. Furthermore, each crystal in a pair should be mounted on substrates cut from the same larger piece of material. Such precautions sufficiently reduce the frequency differences between transmitting and receiving crystals, which with imperfectly matched crystals could otherwise lead to a false alarm that air is in the cassette.

Figure 9:
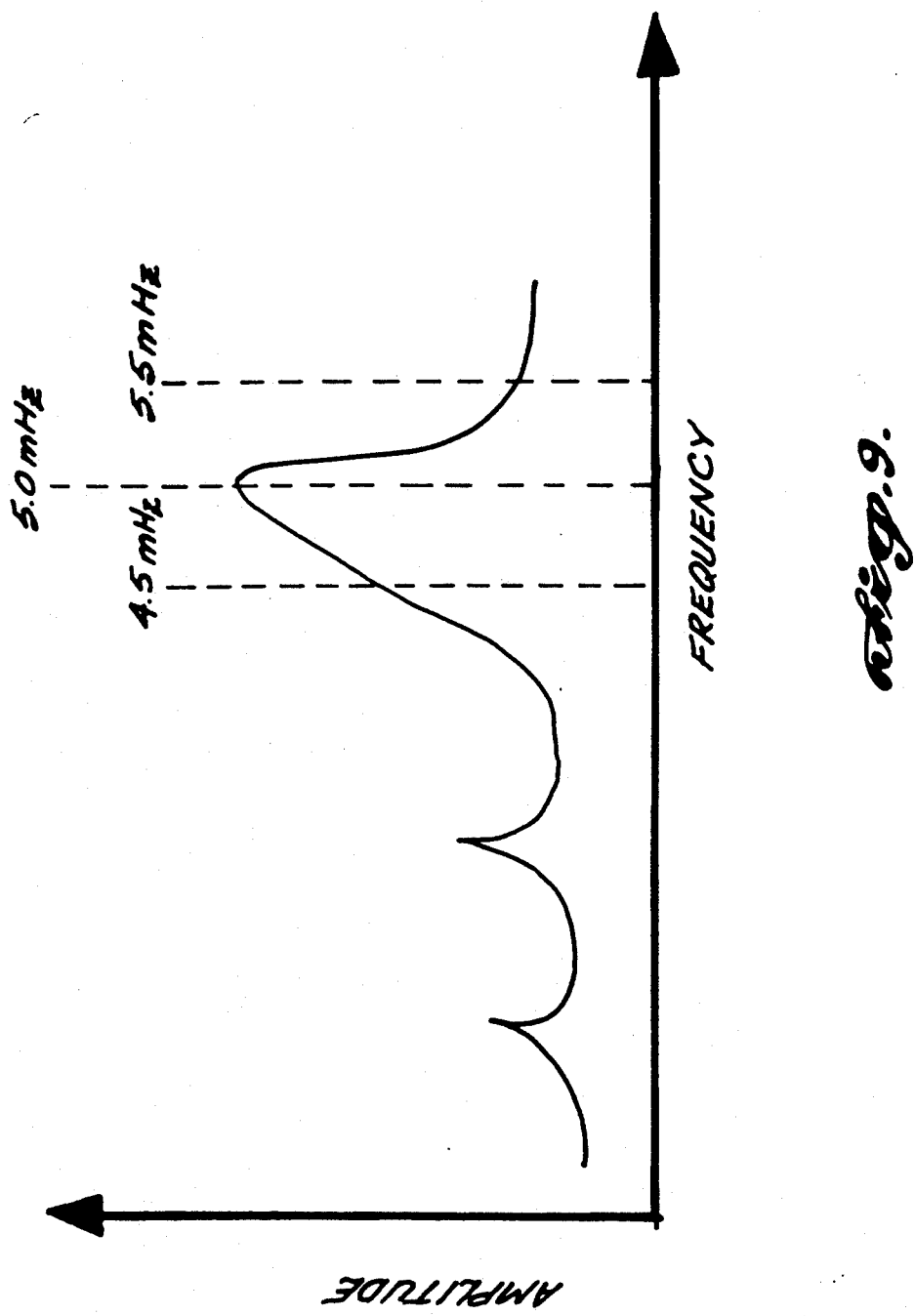
FIG. 9 is a graph of the frequency response of a piezoelectric crystal.

However, a problem arises in that the resonant frequency of each pair of transmitting and receiving crystals can vary from crystal pair to crystal pair. FIG. 9 shows the frequency response of a given crystal having a 5 MHz peak resonating frequency as well as several lower resonating frequencies. As shown in FIG. 9, for example, the pairs are selected from materials which have nominal peak frequencies of about 5 MHz, but the peak frequencies can vary as much as ±20 percent (i.e., 4.00-6.00 MHz), thus, the circuitry to resonate the crystals must be capable of resonating any selected pair within this range if one wishes to avoid having to calibrate each circuit to each pair of crystals. This individual calibration would be extremely laborious.

Sweep oscillator 300 varies the frequency of the electrical signal applied to the transmitting crystals (72 and 72'') over this relatively broad frequency spectrum (i.e., 5 MHz ±20%). It has been observed that this spectrum includes the resonant frequencies of the pairs of crystals 72 and 72' and 72'' and 72''' which will be installed in the cassette driver. In other words, sweep oscillator 300 will hit a frequency for each pair of crystals which produces a sufficient response to avoid false signals. In other words, the frequency of the electrical signal applied to the matched pair of crystals is varied across the range between 4.00 and 6.00 MHz (i.e., a range is swept). In the swept range there will be an intermediate frequency where the transmitting crystal will emit acoustic signals having an amplitude sufficient to excite the receiving crystal. This avoids the false alarm situation where the transmitting crystal is resonated at a frequency which is sufficiently different from its natural peak resonant frequency to "fool" the system that air is in the cassette.

Voltage controlled oscillator (VCO) 301 consists of a 74HC4046 phase locked loop oscillator U1 with only the voltage controlled oscillator section being used. VCO 301 output is coupled by capacitor $C_6$ to the transmitting crystal drivers $Q_1$ and $Q_2$.

VCO 301 is driven by triangle wave oscillator (TW Oscillator) 301a formed by an amplifier U2 with capacitor $C_9$ and resistors $R_{13}$-$R_{16}$. TW Oscillator 301a uses an exclusive OR gate inside VCO 301 as a voltage buffer which improves the symmetry of its output waveform.

TW Oscillator 301a has a frequency of about 3 kHz and a peak-to-peak amplitude of about 1.0 volt with an average value of 2.5 volts. This causes VCO 301 to sweep over a 2 MHz range, covering the required 4.00 to 6.00 MHz range plus to allow component tolerances in the oscillator.

The "timing elements" of VCO 301, namely resistor $R_2$ and capacitor $C_{10}$ are selected so that the sweep range of VCO 301 includes frequencies at which the ceramic material used for the transmitting and receiving crystals will resonate. Thus, if crystal 72 has a resonant frequency of 4.9 MHz, and crystal 72'' has a resonant frequency of 5.3 MHz, both will emit burst of ultrasonic energy that will be detected by the complementary receiving crystals 72' and 72'''.

Line A from VCO 301 is bifurcated into lines B and C, each of which applies the signals generated by VCO 301 to an amplifier circuit 302 or 302', each of which is indentical to the other. Each amplifier circuit 302 or 302' (described in detail below) amplifies the signal to identical 10 volt peak-to-peak sine wave voltage signals at lines 76 and 76', respectively. The frequency of the signal at lines 77 and 77' will vary within the range of sweep oscillator 300.

Amplifier circuit 302 includes a transistor $Q_1$. Transistor $Q_1$ together with resistors $R_3$, $R_4$, and $R_5$, capacitors $C_1$ and $C_2$, and coil $L_1$ form a Class C amplifier. Thus, $L_1$, $C_1$ and the crystal 72 form a tuned load, nominally resonant at 5 MHz. However, the actual resonance of this tuned load varies for reasons explained above. Crystal 72 is a Valpey-Fisher PZT-5H or a Murata P7 piezoelectric crystal.

The amplifier circuit 302' is identical to circuit 302 with $Q_1'$, $R_3'$, $R_4'$, etc. corresponding to $Q_1$, $R_3$, $R_4$, etc. Amplifier circuit 302 applies a high, variable frequency sine wave signal through line 77 to one side of piezoelectric crystal 72 of ultrasonic generator 54 of air-in-line detector 26. The other side of crystal 72 of ultrasonic generator 54 is connected to a 5 volt power supply (not shown) by line 78. The 5 MHz signal applied across crystal 72 excites crystal 72 to generate a high, variable frequency ultrasonic signal across the gap between ultrasonic generator 54 and the ultrasonic receiver 56.

As previously indicated, when there is fluid in the fluid path in air-in-line detector 26, the ultrasonic signal generated is received virtually unattenuated by ultrasonic receiver 56. However, the high frequency sound generated by ultrasonic generator 54 is greatly attenuated if air is present in air-in-line detector 56.

Transistor $Q_2$ and resistors $R_{12}$, $R_{11}$, $R_{10}$, $R_6$, and $R_8$, and capacitor $C_3$ form an AC coupled common emitter amplifier 304. Amplifier 304 is coupled to crystal 72' of receiver 54. Capacitor $C_4$ is an output coupling capacitor which is coupled to transistor $Q_3$. Transistor $Q_3$ forms a threshold voltage detector 306 with resistor $R_7$ and capacitor $C_8$.

When fluid is in air-in-line detector 26 crystal 72' is excited by one or more of the acoustic frequencies generated by crystal 72. The voltage signal received from amplifier 304 at the base of $Q_3$ is a sine wave having a 100 to 200 mV peak. Amplifier $Q_3$ increases that voltage to a sufficient level to cross the threshold formed by the base-emitter forward voltage at $Q_3$. Thus, the output voltage at $Q_3$ collector indicates the presence of fluid.

When air is in air-in-line detector 26, crystal 72' will not be excited by any of the frequencies generated by crystal 72. The signal received at the base of $Q_3$ falls below that necessary to cross the base-emitter threshold of $Q_1$. The output voltage at $Q_3$ collector indicates the presence of air. $Q_3$ collector is coupled to the microprocessor which detects the difference in voltage between the water/air situations.

Figure 10:
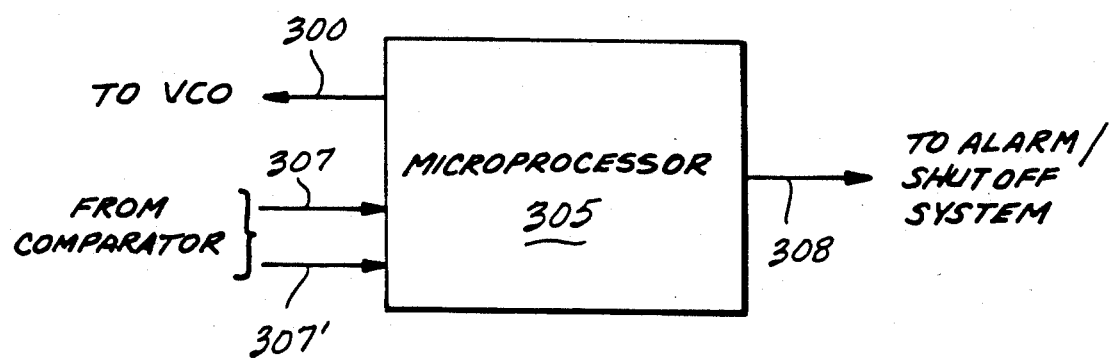
FIG. 10 is a block diagram of a microprocessor used to control and monitor the air-in-line detector circuit of this invention.

FIG. 10 depicts in block diagram a microprocessor 305 used to control the air-in-line detection circuit 298 and monitor the output therefrom. As will be discussed in greater detail hereinafter, microprocessor 305 periodically asserts a VCO-on signal over an oscillator control line 306 to VCO 301. The VCO-on signal triggers the generation of an AC signal by VCO 301, which excites transmitting crystals 72 and 72" to emit bursts of ultrasonic energy. Microprocessor 305 receives the output from $Q_3$ and $Q_3'$ through a pair of sensor input lines 307 and 307', respectively. When the VCO 301 is triggered to oscillate, if either $Q_3$ or $Q_3'$ assert a signal that indicates excess air in the line, microprocessor 305 asserts a signal on an alarm line 308 to trigger the appropriate annunciators and shut-off valves.

In some embodiments of the invention, the signals from $Q_3$ and $Q_3'$ are supplied to comparators (not illustrated). Reference voltages are applied to the comparators that are identical to the voltages that would appear across $Q_3$ and $Q_3'$ when the maximum-amount-of-air/-minimum-amount-of-fluid is sensed by detectors 26 and 28. Depending on the voltages from $Q_3$ and $Q_3'$, the comparators assert either fluid-in-line or air-in-line signals over sensor input lines 307 and 307' to the microprocessor 305. If an air-in-line signal is asserted, microprocessor 305 asserts an appropriate signal on alarm line 308.

Figure 11:
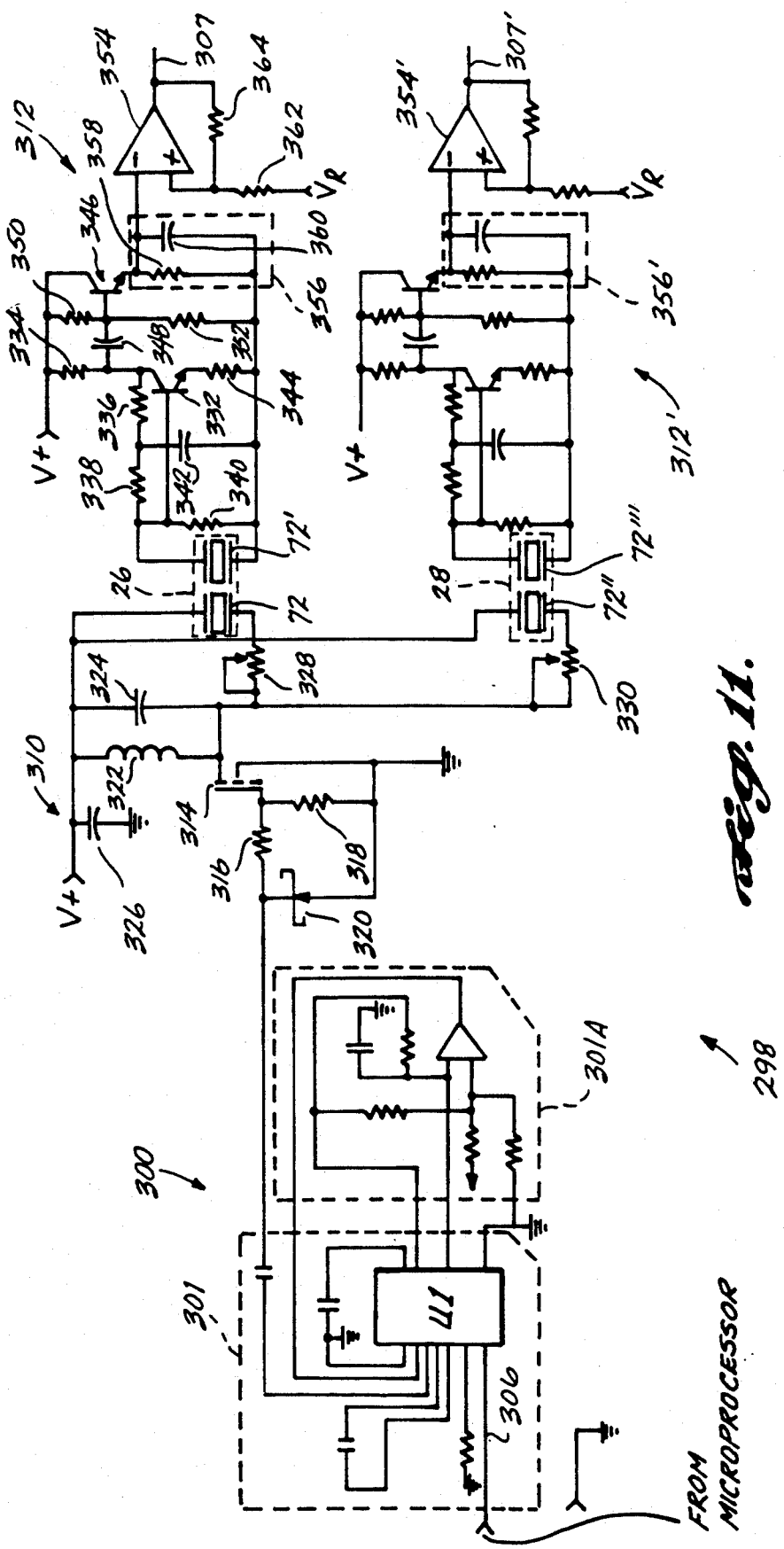
FIG. 11 is a schematic diagram of an alternative embodiment of an air-in-line detection circuit of this invention.

An alternative air-in-line detection circuit 298' is depicted in FIG. 11. The circuit 298' includes the sweep oscillator 300 previously described with respect to FIG. 8 for supplying a variable frequency signal. An alternative amplifier circuit 310 is driven by the output signal from the sweep oscillator 300 and generates drive signals that are input to the transmitting crystals 72 and 72". Air-in-line detection circuit 298' further includes a pair of essentially identical sensor circuits 312 and 312' for generating signals indicative of the air/fluid state sensed by detectors 26 and 28, respectively.

Amplifier circuit 310 includes an enhancement-type MOSFET transistor 314 that is driven by the output signal of the sweep oscillator 300 applied through a resistor 316. Transistor 314 is biased by a resistor 318 extending between the ground and the source. A reverse-biased Schottky diode 320 is tied between the input end of resistor 316 and source terminal of transistor 314 to clamp the negative voltage excursion of the gate of transistor 314 to a maximum of −0.3 volts. This prevents damage to the phase locked loop oscillator U1 that could otherwise result from large negative transient voltages that develop in the below-discussed tank circuit.

The output of transistor 314 is applied to a tank circuit comprising an inductor 322 and a capacitor 324 connected in parallel. Inductor 322 and capacitor 324 are selected so that the signal developed across the tank circuit has the appropriate characteristics to excite the transmitting crystals 72 and 72" into emitting ultrasonic energy sufficient to stimulate sensor circuits 312 and 312' into generating signals of appropriate magnitude. In one embodiment of the invention, inductor 322 and capacitor 324 are selected so that a 20 Vpp signal can be developed thereacross. An appropriate DC power supply, not illustrated, is coupled to the second end of the tank circuit. One or more filter capacitors 326 (one illustrated), are connected to the output from the power supply, as may be required.

Drive signals are supplied from the tank circuit to the transmitting crystals 72 and 72' through parallel-connected variable resistors 328 and 330 respectively. The variable resistors 328 and 330 are used to control the voltages of signals applied to transmitting crystals 72 and 72". Variable resistors 328 and 330 thus allow the circuit 298' gain to be set at a specific DC voltage level across the sensor circuits 312 and 312' for the situations when the cassette 10 is filled with fluid and there is maximum ultrasonic coupling between the transmit and receive crystals.

Sensor circuit 312 is controlled by the signals developed across receiver crystal 72' in response to the ultrasonic energy received thereby. Sensor circuit 312 includes a bipolar transistor 332 driven by signals developed across receiver crystal 72'. A power supply, not illustrated, supplies a collector voltage to transistor 332 through a resistor 334. Transistor 332 is biased by series-connected resistors 336 and 338 that are connected between the transistor's collector and base, and a resistor 340 which is connected between the base and emitter of the transistor. A capacitor 342 tied between the junction of resistors 336 and 338 and ground filters AC signals from the bias voltage. Transistor 332 is emitter-biased by a resistor 344 extending between the emitter and ground.

Signals produced by the transistor 332 are applied through an AC coupling capacitor 348 to a transistor 346 that is part of an AM detector. Transistor 346 is biased by a resistor 350 connected between the power supply and its base and a resistor 352 connected between the base and ground. Resistors 350 and 352 are selected so that a minimal positive voltage biases transistor 346 into conduction. The output signal from transistor 346 is demodulated across a resistor 358 and a capacitor 360 that are both tied to ground. Resistor 358 and capacitor 360 are also selected to function as a quick charge-slow discharge peak followers 356. These characteristics desensitize the circuit 298' to small bubbles that inevitably form in the fluid and that do not affect the safety of the IV delivery system.

The signal from peak follower 356 is applied to a comparator 354 that asserts a signal indicating whether circuit 298' has detected air or fluid across detector 26. The signal from peak follower 356 is compared with a reference voltage, Vr, which is the expected voltage that is developed across the peak follower when the minimum acceptable amount of fluid is in fluid passage 40 (FIG. 3). In the depicted embodiment, comparator 354 asserts a low "fluid-in-line" signal whenever sufficient fluid is in the fluid passage, and a high "air-in-line" signal whenever there is too much air in the fluid passage. A resistor 362, tied between the positive input of the comparator 354 and the reference voltage source, and a resistor 364, tied between the output of the comparator and the positive input, provide positive feedback that results in 20 mV of hysteresis at the comparator threshold so as to minimize noise in the output signal. The output signal from comparator 354 is applied to the microprocessor 305 over sensor input line 307.

Sensor circuit 312', which is responsive to signals developed across receiving crystal 72''', is identical to sensor circuit 312 and, accordingly, will not be described in detail. The only difference between sensor circuits 312 and 312' is in the reference voltages applied to their comparators 354 and 354', respectively. Ultrasonic detector 26, the empty detector, is primarily used to monitor whether the IV container and associated fluid line are empty. Since detector 26 is between the IV container and a pumping chamber (not illustrated) in the cassette 10, sensor circuit 312 does not have to assert air-in-line signals when smaller bubbles are in the fluid passage 40. Accordingly, an appropriate reference voltage is applied to comparator 354 so that it asserts an air-in-line signal only when large bubbles are detected that indicate the source container is about empty. In one embodiment of the invention, the reference voltage applied to comparator 354 is approximately 500 mV, which is approximately one-fifth of the fluid filled voltage level. Ultrasonic detector 28 is used to monitor the fluid infused into the patient and sensor circuit 314' thus is set to be more sensitive to smaller bubbles. Accordingly, a low reference voltage, 300 mV, which is approximately one-fifth of the fluid filled voltage level, is applied to comparator 354' so that when smaller bubbles are in the fluid passage 40, air-in-line signals will be asserted.

FIGS. 12A-G are timing diagrams of the signals asserted during operation of the air-in-line detection circuit 298'. As depicted in FIG. 12A, TW oscillator 301a is always active and constantly generates a triangular wave. In 3 one embodiment of the invention, TW oscillator generates an output signal centered at 2.5 V with a 2.0 V peak-to-peak amplitude and a frequency of approximately 3K Hz.

Microprocessor 305 periodically asserts a VCO-on signal represented by the "low" signal depicted in FIG. 12B. The frequency with which the VCO-on signal is asserted depends on the specific use of the invention. For example, when the ultrasonic detector is used with a plunger-type IV fluid pump (not illustrated), the VCO-on signal is asserted simultaneously with the depression of the pump plunger so that an air-in-line measurement occurs simultaneously with the pumping of fluid through the fluid passages 40 (FIG. 3). The VCO-on signal is asserted for a selected time so that if there is sufficient fluid in the fluid passages 40, consequential bursts of ultrasonic energy received by the receiving crystal-sensor circuit subassemblies induce voltages that fully charge the peak followers 356 and 356'. In practice, at least 5 to 10 bursts of ultrasonic energy from transmitting crystals 72 and 72' are normally needed to fully charge the peak follower 356 and 356', respectively. In the described embodiment, the VCO-on signal is asserted for approximately 1 millisecond.

When the VCO-on signal is asserted, VCO 301 generates an AC signal as represented by FIG. 12C. The triangular wave signal driving VCO 301 causes the oscillator to generate a variable frequency output signal within the normal resonant frequency range of the transmitting crystals 72 and 72". For transmitting crystals having a nominal peak frequency of 5 MHz, VCO 301 generates an output signal having a frequency sweep between 4 and 6 MHz.

Output signals from VCO 301 centered around the resonant frequencies of transmitting crystals 72 and 72" causes periodic bursts of ultrasonic energy therefrom as represented in FIG. 12D. The bursts of ultrasonic energy are transmitted through the fluid passages 40 to the receiving crystals 72' and 72'''. The received energy causes voltages to be periodically developed across receiving crystals 72' and 72''' so that, in turn, voltages are developed across the peak followers 356 and 356' of the sensor circuits 312 and 312' as depicted by FIG. 12E. When there are sufficient amounts of fluid in fluid passages 40, the voltages developed across peak followers 356 and 356' are greater than the corresponding reference voltages. Comparators 354 and 354' assert fluid-in-line signals represented by the low signal of FIG. 12F. When there is sufficient fluid in the passages, the peak followers rapidly charge and the comparators 354 and 354' assert fluid-in-line signals several microseconds after the VCO-on signal is asserted. After the VCO-on signal is negated, peak followers 356 and 356' maintain their voltages above the reference voltages until they discharge, with a 4.7 millisecond time constant. Comparators 354 and 354' thus assert fluid-in-line signals for a similar amount of time after the VCO-on signal is negated.

As indicated by arrow 370 in FIG. 12g, microprocessor 305 is programmed to monitor the signals from comparators 354 and 354' simultaneously with the negation of the VCO-on signal. If there is sufficient fluid in the passages, comparators 354 and 354' will assert fluid-in-line signals as described. If there are a significant number of bubbles in either fluid passage 40, the ultrasonic energy received by the receiving crystal 72' or 72" is noticeably attenuated. The voltage developed across the peak follower 356 or 356' is then below the appropriate reference voltage, and comparator 354 or 354' asserts an air-in-line signal. In response to the asserted air-in-line signal, microprocessor 305 (FIG. 10) asserts an appropriate signal on alarm line 308.

In the embodiment of the invention used with a plunger pump, ultrasonic detectors 26 and 28 are monitored in 5 millisecond cycles, the rate at which the plunger makes downward strokes. During each cycle, the VCO-on signal is asserted for one millisecond, the signals from the comparators 354 and 354' are briefly monitored, and there is a four millisecond pause before the start of a new cycle. When an air bubble starts to transit between one of the detectors 26 or 28, the peak follower 356 or 356' may not discharge to a level below the reference voltage during the four millisecond pause. Accordingly, during the subsequent monitoring period, comparator 354 or 354' may assert a fluid-in-line signal even though a bubble is present. However, the minimum transit time for bubbles across an ultrasonic detector 26 or 28 is about 100 milliseconds. Thus, when a bubble is present, it attenuates the ultrasonic energy detected by the sensor circuit 312 or 312' during several consecutive monitoring periods. During at least the latter monitoring periods, the peak follower 356 or 356' is discharged below the reference voltage and the comparator 354 or 354' asserts an air-in-line signal. Thus, bubbles do not escape detection even though the fluid passages are not continuously monitored.

Microprocessor 305 also determines whether or not the air-in-line detection circuit 298' is operating properly. The test is performed by monitoring the signals asserted by the comparators after the VCO-on signal has been negated. As depicted by arrow 372 in FIG. 12G, the monitoring is done at least 10 milliseconds after the VCO-on signal is negated, so that the peak followers 356 and 356' have had time to fully discharge. If the detector circuit 298' is operating properly, the signals across peak followers 356 and 356' should be below the reference voltage levels, and comparators 354 and 354' should assert air-in-line signals. If fluid-in-line signals are asserted, there is a malfunction in the detection circuit 298', and microprocessor 305 asserts an appropriate signal on alarm line 308. The test is normally performed when an IV container is first attached to the pump-detector assembly or other times when it is known there is fluid in the passages 40. Tests are performed at these times because it is desirable to verify that the circuit 298' does indeed switch from asserting fluid-in-line signals to asserting air-in-line signals after the VCO-on signal is negated.

The above-discussed polarities, voltages, time constants and frequencies describe the signals asserted during operation of the second air-in-line detection circuit 298'. It is understood that the signals asserted during the operation of the first-described air-in-line detection circuit 298 have similar characteristics to those described, since the two circuits 298 and 298' have the same basic principles of operation. Differences in asserted signals during the operation of the different air-in-line detection circuits 298 and 298' merely reflect the different construction of the circuits.

The VCO 301 of the sweep oscillator 300 of this invention generates a variable frequency output signal, a portion of which excites the transmitting crystals 72 and 72' into releasing bursts of ultrasonic energy. This technique eliminates the need to provide the detector circuit with a finely tuned oscillator to excite the transmitting crystals precisely at their resonant frequency. Moreover, the sweep oscillator excites both transmitted crystals 72 and 72" into releasing ultrasonic energy even though the crystals may have different resonant frequencies. This eliminates having to provide individual drive circuits for the separate ultrasonic detectors 26 and 28.

Still other advantages are associated with the second detection circuit 298' of this invention. Transistor 314 in amplifier circuit 310 switches off current flow in the amplifier circuit 310 when VCO 301 is not triggered to oscillate. Thus, the amplifier circuit 310 uses a minimal amount of current, which makes it well suited for use with portable, battery-powered IV pumping and bubble detection systems. The single amplifier circuit 310 supplies signals for driving the multiple transmitting crystals so as to minimize both the cost and size of the detection circuit. Variable resistors 328 and 330 provide a convenient means for limiting the energy applied to receive crystals 72' and 72''', which is useful for preventing sensor circuits 312 and 312' from being overdriven.

Air-in-line detection circuit 298' is also well-suited for use in high electrical and sonic noise environments such as hospitals. Feedback resistors 336 and 338 stabilize the operating point of sensor circuit transistor 332 so that collector voltage swings thereacross can approximate the supply voltage. This makes it possible to adjust the detection circuit 298' so that the presence of fluid in fluid passage 40 results in high, readily distinguishable voltages being developed across transistor 332 and in turn across peak detector 356. The reference voltage can thus be set to a relatively high level so that low voltage noise signals that develop across transistor 332 do not cause comparator 354 to assert a false fluid-in-line signals. Moreover, AM detector transistor 346 provides the sensor circuit 312 output signal with a near-linear received ultrasonic energy-output voltage profile. This approach facilitates applying a reference voltage to the comparator 354 that accurately reflects the sensor circuit voltage when a minimum acceptable amount of fluid is detected.

It should be understood that this description of the preferred embodiments of the invention is for the purpose of illustration only. It should be apparent that this invention can be practiced using diverse circuitry or in systems that use different circuitry than is disclosed in this specification, with the attainment of some or all of the advantages of this invention. For example, the transmitting circuit 302 and receiving amplifier circuit 304 of the first air-in-line detection circuit 298 may be interchanged with the amplifier circuit 310 and sensor circuits 312 and 312' of the second air-in-line detection circuit 298' as desired. A sweep oscillator substantially different from the one described may be used to provide the variable frequency signals that drive the transmitting crystals 72 and 72".

Still other embodiments of the invention may be provided wherein the peak detectors 356 and 356' are eliminated from sensor circuits 312 and 312' so that the comparators 354 and 354' assert signals that are near-instantaneous representations of the detected air/fluid state. In these embodiments of the invention, VCO 301 would most likely be triggered to continually provide a drive signal to the transmitting crystals 72 and 72" and the output signals from the comparators 354 and 354' would most likely be monitored continually. Other alternative circuit constructions are, of course, possible. For example, if a higher drive level voltage is applied to the receiving crystals 72' and 72''', the sensor circuit may comprise an RF-type autotransformer followed by a detector. Furthermore, while the disclosed air-in-line detector circuits 298 and 298' can be used in conjunction with two complementary ultrasonic detectors 26 and 28, it is readily understood that the circuits of this invention can be used with one, three or more ultrasonic detectors as may be required in any particular embodiment of the invention. Therefore, it is the object of the appended claims to cover all such modifications and variations as come within the true spirit and scope of the invention.

The embodiments of the invention in which an exclusive property or privilege is claimed are defined as follows:

1. A device for detecting the presence of liquid-state fluid in a conduit, comprising:
   (a) acoustic transmitter means for generating acoustic signals across the conduit, said acoustic transmitter means generating said acoustic signals in response to a drive signal at a selected frequency applied thereto;
   (b) signal generating means for applying a drive signal to said acoustic transmitter means, said signal generator means continuously generating said drive signal over a sweep range of frequencies including said acoustic transmitter drive signal selected frequency so as to cause said acoustic transmitter means to periodically emit said acoustic signals; and
   (c) acoustic receiver means responsive to said acoustic signals emitted by said acoustic transmitter means, for producing a signal indicative of whether or not liquid-state fluid is present in the conduit wherein said signals indicative of the presence of liquid-state fluid is periodically produced when said acoustic signals are received.

2. The device for detecting the presence of fluid of claim 1, wherein said signal generating means comprises a sweep oscillator generating an output signal over said sweep range of frequencies, and an amplifier coupled to said sweep oscillator so as to receive said output signals, and in response thereto, producing said signal generator drive signal.

3. The device for detecting the presence of fluid of claim 2, wherein said sweep oscillator includes a voltage controlled oscillator, and a triangle wave oscillator that applies a varying voltage signal to said voltage controlled oscillator, whereby said variable voltage signal causes said voltage controlled oscillator to generate said sweep oscillator output signal.

4. The device for detecting the presence of fluid of claim 2, wherein said sweep oscillator selectively generates said sweep frequency range output signal, and said amplifier includes a switch responsive to said oscillator output signal, for allowing current flow through said amplifier only when said swept frequency range output signal is generated.

5. The device for detecting the presence of fluid of claim 4, wherein:
   (a) said sweep oscillator generates said sweep frequency range output signal in response to an oscillator-on signal;
   (b) said acoustic receiver means generates a fluid-in-line signal whenever said acoustic signal is emitted from said acoustic transmitter means and there is at least a selected amount of liquid in the conduit; and
   (c) further including processor means connected to said sweep oscillator for periodically transmitting said oscillator-on signal thereto, and connected said acoustic receiver means for receiving said fluid-in-line signal, and operative when said oscillator-on signal is transmitted and said fluid-in-line signal is not received, to transmit an alarm signal so as to cause actuation of an alarm.

6. The device for detecting the presence of fluid of claim 5, wherein said test is performed by said processor means at selected times after said process means has completed transmitting said oscillator-on signal and after said fluid-in-line signal has been transmitted.

7. The device for detecting the presence of fluid of claim 4, wherein:
   said sweep oscillator selectively generates said sweep frequency range output signal in response to a signal generator-on signal;
   said acoustic transmitter means periodically generates said acoustic signals when said amplifier produces said signal generator drive signal at said acoustic transmitter drive signal frequency;
   said acoustic receiver means generates a fluid-in-line signal after a selected number of said acoustic signals are emitted and there is a selected amount of liquid in the conduit; and
   further including processor means connected to said signal generator means for periodically transmitting said signal generator-on signal thereto, and connected to said acoustic receiver means for receiving said fluid-in-line signal, and operative at a selected time when said generator-on signal is transmitted and said fluid-in-line signal is not received, to generate an alarm signal so as to actuate an alarm.

8. The device for detecting the presence of fluid of claim 1, wherein:
   (a) said acoustic transmitter means includes a first transmitter that is responsive to acoustic transmitter drive signals at a first selected frequency, and a second transmitter that is responsive to acoustic transmitter drive signals at a second selected frequency, said first and second selected frequencies being different;
   (b) said receiver means includes a plurality of acoustic receivers, each being responsive to acoustic signals emitted by one of said plurality of acoustic transmitters; and
   (c) said signal generator means is operative to apply said drive signal to each of said acoustic transmitters and operative to generate said drive signal over said sweep range of frequencies, said sweep range of frequencies including said acoustic transmitter drive signals at said first and second selected frequencies.

9. The device for detecting the presence of fluid of claim 8, wherein said signal generator means comprises a sweep oscillator generating an output signal over said swept range of frequencies, and signal amplifier means coupled to said sweep oscillator so as to receive said output signals therefrom and in response thereto, generating said signal generator drive signal.

10. The device for detecting the presence of fluid of claim 9, further including separate attenuation means attached between said amplifier means and each of said acoustic transmitters for controlling the magnitude of said drive signal applied to said acoustic transmitter.

11. The device for detecting the presence of fluid of claim 1, wherein:
(a) said signal generation means selectively generates said drive signal in response to a signal generator-on signal;
(b) said acoustic receiver means generates a fluid-in-line signal when said acoustic signal is emitted and there is a selected amount of liquid in the conduit; and
(c) further including processor means connected to said signal generator means and periodically transmitting said signal generator-on signal thereto, and connected to said acoustic receiver means for receiving said fluid-in-line signal, and operative when said generator-on signal is transmitted and said fluid-in-line signal is not received, to transmit an alarm signal to cause actuation of an alarm.

12. The device for detecting the presence of fluid of claim 11, wherein said processor means is further operative to test said acoustic transmitter means, said generator means, and said acoustic receiver means by selectively monitoring signals from said acoustic receiver means when said signal generator-on signal is not transmitted, and if said fluid-in-line signal is then received, to transmit an alarm signal so as to cause actuation of an alarm.

13. The device of detecting the presence of fluid of claim 12, wherein said test is preformed by said processor means at a selected time after said processor means stops transmitting said signal generator-on signal, and after said fluid-in-line signal has been transmitted.

14. The device for detecting the presence of fluid of claim 13, wherein said processor means is operative to test said acoustic transmitter means, said sweep signal generating means, and said acoustic receiver means by selectively monitoring signals from said acoustic receiver means when said oscillator-on signal is not transmitted, and if said fluid-in-line signal is then received, to transmit an alarm signal so as to cause actuation of an alarm.

15. The device for detecting fluid of claim 1, wherein said acoustic receiving means comprises:
(a) a receiver transducer for receiving said acoustic signals and generating a receiver transducer signal in response to the magnitude of said received acoustic signals;
(b) amplifier means coupled to said receiver transducer, for generating an output signal proportional to said receiver transducer signal; and
(c) AM detector means coupled to said amplifier means, for receiving said amplifier output signal therefrom, and in response thereto producing a detector signal having a voltage proportional to the magnitude of said amplifier output signal.

16. The device for detecting fluid of claim 15, wherein said amplifier output signal is applied to said AM detector through an AC coupling capacitor.

17. The device for detecting fluid of claim 15, further including a comparator for receiving said AM detector signal and comparing it to a reference voltage, said comparator transmitting a fluid-in-line signal in response to the difference between said detector signal voltage and said reference voltage.

18. The device for detecting fluid of claim 15, wherein said AM detector means includes a slow-discharge peak follower circuit.

19. The device for detecting the presence of fluid of claim 1, wherein said signal generator means comprises:
a sweep oscillator generating an output signal over said sweep range of frequencies, said sweep oscillator generating said signal in response to a signal generator-on signal produced by a detector control circuit; and
an amplifier including at least one amplifying element connected to a power source, for producing said acoustic transmitter drive signals and a switch connected to said amplifying element for selectively controlling current flow through said amplifying element and connected to said sweep oscillator for receiving said oscillator output signal, said switch being responsive to said oscillator output signal, whereby, when said oscillator output signal is not produced, the switch interrupts current flow through said amplifying element.

20. The device for detecting the presence of fluid of claim 19, wherein said amplifier includes a tank circuit connected to the power supply and a field-effect transistor connected to said tank circuit to control current flow therethrough, said field-effect transistor being further connected to said sweep oscillator for receiving said oscillator output signal so that said oscillator output signal gates said field-effect transistor.

21. The device for detecting the presence of fluid of claim 20 wherein said field effect transistor is connected between said tank circuit and ground.

22. An ultrasonic detector for monitoring the presence of liquid-state fluid in a conduit, comprising:
(a) an acoustic transmitter for generating acoustic signals across the conduit, said acoustic transmitter generating said acoustic signals in response to a drive signal at a selected frequency applied thereto;
(b) an acoustic receiver responsive to said acoustic signals generated by said acoustic transmitter for producing a signal indicative of whether or not liquid-state fluid is present in the conduit, wherein said signal indicative of the presence of liquid-state fluid is periodically produced when said acoustic signals are received; and
(c) a signal generator for applying a drive signal to said acoustic transmitter including a sweep oscillator for continuously generating an output signal over a swept range of frequencies including said acoustic transducer selected frequency and an amplifier coupled to said sweep oscillator for receiving said oscillator output signals and, in response thereto, producing said drive signal for application to said acoustic transducer signal so as to cause said acoustic transmitter to periodically emit said acoustic signals, wherein said amplifier includes an amplifying element connected to a power supply and a switch for selectively controlling current flow through said amplifying element, said switch being responsive to said oscillator output signal, whereby, when said oscillator output signal is not produced, the switch interrupts current flow through said amplifying element.

23. The ultrasonic detector of claim 22, wherein said amplifying element is a tank circuit.

24. The ultrasonic detector of claim 23, wherein said switch is a field-effect transistor connected to said sweep oscillator so that said sweep oscillator gates said transistor and connected between said tank circuit and ground to selectively connect said tank circuit to ground in response to receipt of said oscillator output signal.

25. The ultrasonic detector of claim 22, wherein said switch is a field-effect transistor connected to said sweep oscillator so that said sweep oscillator gates said transistor and connected between said amplifying element and ground to selectively connect said amplifying element to ground in response to receipt of said oscillator output signal.

26. An ultrasonic detector for monitoring the presence of liquid-state fluid in a conduit, comprising:
(a) at least two spaced-apart acoustic transmitters for generating acoustic signals across the conduit, including a first acoustic transmitter that generates acoustic signals in response to a first drive signal at a first selected frequency and a second acoustic transmitter that generates acoustic signals in response to a second drive signal at a second selected frequency, wherein said first and second selected frequencies are different;
(b) a plurality of acoustic receivers, each of said receivers being responsive to said acoustic signals generated by a separate one of said acoustic transmitters for producing signals indicative of whether or not liquid-state fluid is present in the conduit, wherein each of said acoustic receivers produces a signal indicative of the presence of liquid-state fluid when said acoustic signals are received; and
(c) a signal generator for applying a drive signal to said acoustic transmitters including a sweep oscillator for continuously generating an output signal over a swept range of frequencies including said first and second selected frequencies and an amplifier coupled to said sweep oscillator for receiving said oscillator output signal and, in response thereto, producing said drive signal for application to said acoustic transducers so as to cause each said acoustic transmitter to periodically emit said acoustic signals.

27. The ultrasonic detector of claim 26, wherein said amplifier includes at least one amplifying element connected to a power source for producing said acoustic transmitter drive signal and a switch connected to said amplifying element for selectively controlling current flow through said amplifying element and connected to said sweep oscillator for receiving said oscillator output signal, said switch being responsive to said oscillator output signal, whereby, when said oscillator output signal is not produced, the switch interrupts current flow through said amplifying element.

28. The ultrasonic detector of claim 27, wherein said amplifier includes a tank circuit connected to the power supply and a field-effect transistor connected to said tank circuit to control current flow therethrough, said field-effect transistor further connected to said sweep oscillator for receiving said oscillator output signal so that said oscillator output signal gates said field-effect transistor. e]

* * * * *

UNITED STATES PATENT AND TRADEMARK OFFICE
CERTIFICATE OF CORRECTION

PATENT NO. : 5,191,795
DATED : March 9, 1993
INVENTOR(S) : G. H. Fellingham et al.

It is certified that error appears in the above-identified patent and that said Letters Patent is hereby corrected as shown below:

| COLUMN | LINE | |
|---|---|---|
| 6 | 66 | "burst" should read --bursts-- |
| 8 | 57 | "crystals 72 and 72' " should read --crystals 72 and 72"-- |
| 9 | 25 | "followers 356" should read --follower 356-- |
| 10 | 11 | after "In" delete "3" |
| 10 | 32 | "follower 356 and 356' " should read --followers 356 and 356'-- |
| 12 | 6 & 7 | "crystals 72 and 72' " should read --crystals 72 and 72"-- |
| 13 | 12 | after "a" insert --Schotty diode-- |
| 13 (Claim 1 | 45 Line 20) | "signals" should read --signal-- |
| 14 (Claim 5 | 12 Line 12) | after "connected" insert --to-- |
| 14 (Claim 9 | 68 Line 4) | "signal" should read --single-- |
| 15 (Claim 10 | 8 Line 5) | "transmitter" should read --transmitters-- |

UNITED STATES PATENT AND TRADEMARK OFFICE
CERTIFICATE OF CORRECTION

PATENT NO. : 5,191,795
DATED : March 9, 1993
INVENTOR(S) : G. H. Fellingham et al.

It is certified that error appears in the above-identified patent and that said Letters Patent is hereby corrected as shown below:

| COLUMN | LINE | |
|---|---|---|
| 15 (Claim 13 | 36 Line 2) | "preformed" should read --performed-- |
| 16 (Claim 19 | 7 Line 1) | "fluid" should read --liquid-- |
| 18 (Claim 28 | 32 Line 8) | after "transistor" delete "el" |

Signed and Sealed this

Thirtieth Day of November, 1993

Attest:

BRUCE LEHMAN

Attesting Officer

Commissioner of Patents and Trademarks